(12) United States Patent
Ouchi

(10) Patent No.: US 6,254,529 B1
(45) Date of Patent: Jul. 3, 2001

(54) ENDOSCOPIC FORCEPS STOPPER

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/288,567

(22) Filed: Apr. 9, 1999

(30) Foreign Application Priority Data

Apr. 14, 1998 (JP) .................................................. 10-102489

(51) Int. Cl.⁷ ....................................................... A61B 1/00
(52) U.S. Cl. .................... 600/154; 600/159; 604/167.01; 604/167.02; 604/167.03
(58) Field of Search ...................... 600/154, 159; 604/167.01, 167.02, 167.03

(56) References Cited

U.S. PATENT DOCUMENTS

| | | |
|---|---|---|
| 4,653,477 | 3/1987 | Akui et al. . |
| 4,715,360 | 12/1987 | Akui et al. . |
| 4,909,798 | * 3/1990 | Fleischhacker et al. ............. 604/256 |
| 5,122,122 | * 6/1992 | Allgood ................................ 604/174 |
| 5,269,771 | * 12/1993 | Thomas et al. ....................... 604/213 |
| 5,300,033 | * 4/1994 | Miller ................................... 604/167 |
| 5,324,270 | * 6/1994 | Kayan et al. ......................... 604/167 |
| 5,385,552 | * 1/1995 | Haber et al. ......................... 604/167 |
| 6,093,176 | * 7/2000 | Dennis ................................. 604/256 |

FOREIGN PATENT DOCUMENTS 7-255665  10/1995  (JP) .

* cited by examiner

Primary Examiner—Linda C. M. Dvorak
Assistant Examiner—Jocelyn Ram
(74) Attorney, Agent, or Firm—Greenblum & Bernstein, P.L.C.

(57) ABSTRACT

A pair of generally semicircular, passage blocking valves (33b) that are made of an elastic material are provided in such a way as to block the passage leading to the inlet of a channel 4 of an endoscope and in such a state that the diameters (33c) of the two blocking valves abut to interfere with each other and that the abutting surfaces of the two blocking valves (33b) are closed in a normal state but are spread apart elastically by the insertion of a treatment tool.

6 Claims, 7 Drawing Sheets

ENDOSCOPIC FORCEPS STOPPER

BACKGROUND OF THE INVENTION

The present invention relates to an endoscopic forceps stopper for preventing the leakage of pressure from the inlet of a treatment tool insertion channel of an endoscope.

Endoscopic forceps stoppers are usually equipped with a passage blocking valve that is made of an elastic material. A slit is generally formed through the passage blocking valve so that the valve can be elastically open upon the insertion of a treatment tool.

Endoscopic forceps stoppers must fulfill two requirements: 1) when no treatment tool is used, the stopper must be closed by itself to prevent the leakage of pressure from the inlet of a treatment tool insertion channel; and 2) when a treatment tool is inserted into the channel, the stopper must be elastically spread open to permit the passage of the treatment tool while preventing the pressure leakage.

However, in practical applications, it is difficult to prevent pressure leakage fully irrespective of whether a treatment tool is used or not. The slightest wear of the stopper around the slit due to the repeated insertion and removal of the treatment tool will lead to extensive pressure leakage when the treatment tool is not used. A detachable sealing cap must be further attached to the stopper to ensure that no pressure leakage will occur when no treatment tool is used, but the addition of the detachable sealing cap involves cumbersome steps to handle.

SUMMARY OF THE INVENTION

An object, therefore, of the present invention is to provide an endoscopic forceps stopper that does not use a cap or any other sealing device, and which yet is capable of positively preventing the pressure leakage when no treatment tool is used and effectively suppressing the pressure leakage when a treatment tool is used.

An endoscopic forceps stopper according to a preferred embodiment of the present invention is designed as follows: A pair of generally semicircular, passage blocking valves that are made of an elastic material are provided in such a way as to block the passage leading to the inlet of a treatment tool insertion channel. The diameters of the two blocking valves abut to interfere with each other. The abutting surfaces of the two blocking valves are closed in a normal state but are spread apart from each other elastically by the insertion of a treatment tool. The endoscopic forceps stopper can dispense with a sealing cap and yet it is capable of positive prevention of pressure leakage when no treatment tool is used while ensuring effective suppression of pressure leakage when a treatment tool is being passed.

The pair of generally semicircular, passage blocking valves may be provided in such a state that the end faces of their diameter are deformed by abutting against each other. The pair of generally semicircular, passage blocking valves may be provided in such a state that their diameters partly overlap each other.

At least one of said pair of passage blocking valves may be detachably provided.

The present disclosure relates to the subject matter contained in Japanese patent application No. Hei. 10-102489 (filed on Apr. 14, 1998), which is expressly incorporated herein by reference in its entirety.

DETAILED DESCRIPTION OF THE ENDOSCOPIC FORCEPS STOPPER

Figure 8:
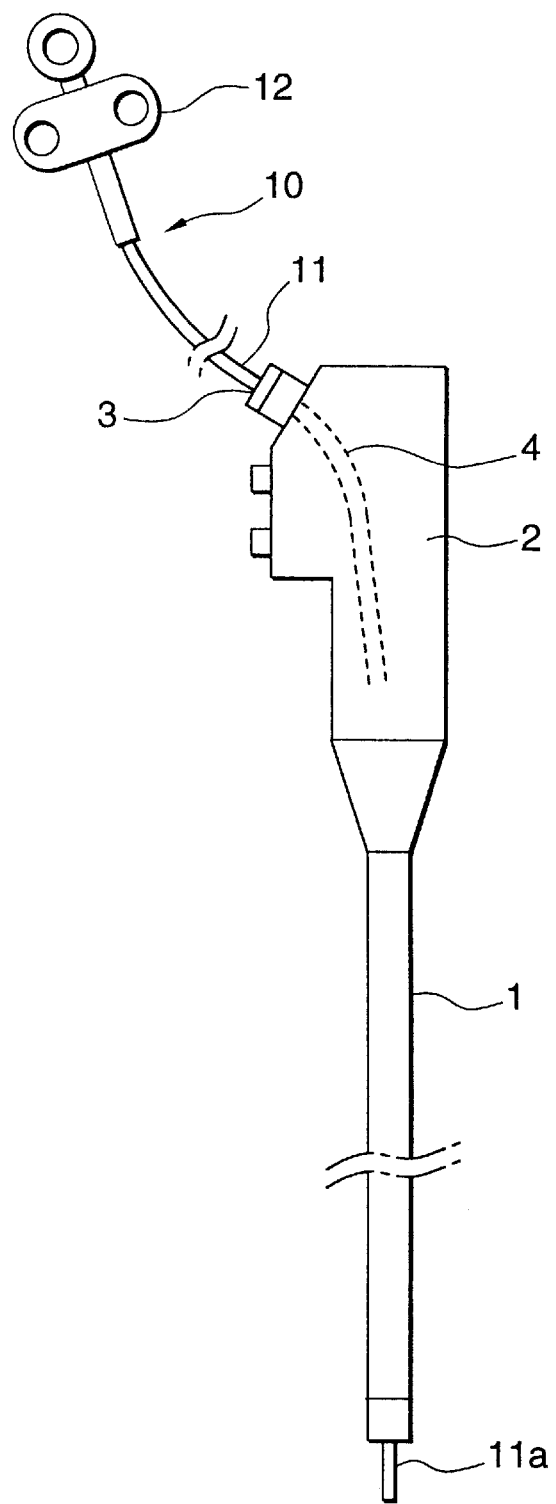
FIG. 8 is a sketch of an endoscope with a treatment tool inserted through an internal channel.

FIG. 8 shows a treatment tool 10 as it has been inserted into the corresponding channel 4 passing through an endoscope. The inserting portion 1 of the endoscope has the basal end connected to the manipulating section 2, and a forceps stopper 3 is mounted on the inlet of the channel 4, which is provided on the manipulating section 2.

The sheath 11 of the treatment tool 10 inserted into the channel 4 has the distal tip 11a projecting forward from the distal end of the inserting portion 1 of the endoscope. Indicated by 12 is a hand operated manipulating section connected to the basal end of the sheath 11.

Figure 1:
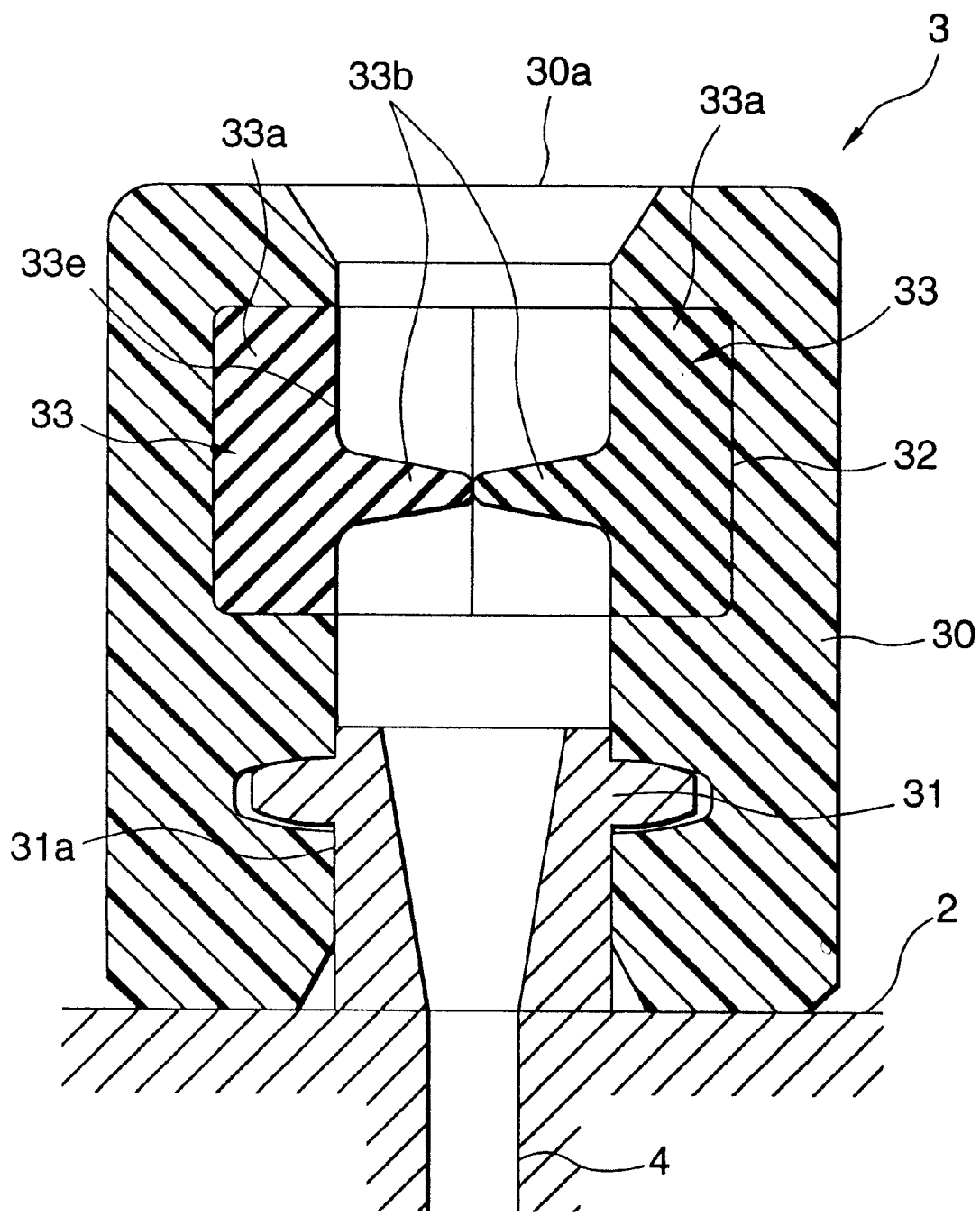
FIG. 1 shows a front section of an endoscopic forceps stopper according to a first embodiment.

FIG. 1 shows a front section of the forceps stopper 3. Indicated by 31 is a treatment tool receiving socket that communicates with the channel 4 and projects from the surface of the manipulating section 2. The socket 31 of this example is shaped like a so-called "lure lock" male socket.

Indicated by 30 is a stopper casing that is formed of a somewhat hard, elastic rubber or plastic material and that is detachably mounted on the treatment tool receiving socket 31. The stopper casing 31a is tightly fitted to the outer circumference 31a of the socket 31 to prevent the leakage of pressure from any gap between the mating surfaces.

The stopper casing 30 has a circular, block member receiving groove 32 formed on the circumference of the area between the opening 30a of the casing 30 and the opening of the socket 31. A pair of passage blocking members 33 made of an elastic material such as silicone rubber, nitrile rubber or chloroprene rubber are fitted into the circular groove 32.

Figure 2:
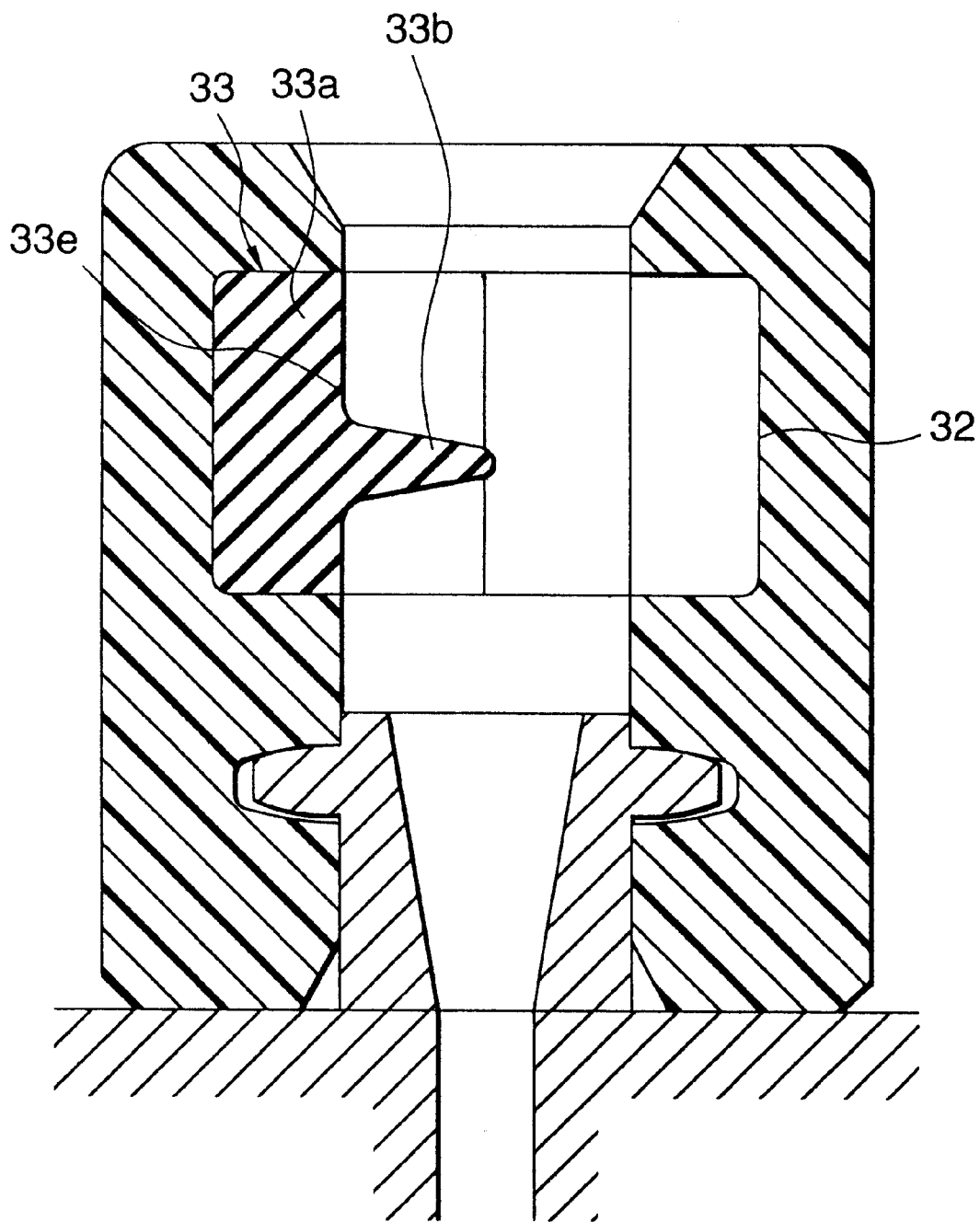
FIG. 2 shows a front section of the endoscopic forceps stopper according to the first embodiment with one of the two passage blocking members being taken away.
Figure 3:
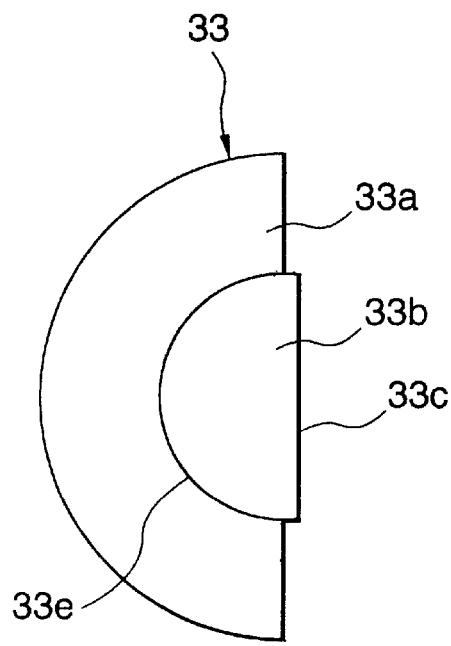
FIG. 3 is a plan view of one element of a pair of passage blocking members used in the first embodiment.

FIG. 2 shows a front section of the forceps stopper 3 with only one passage blocking member 33 being fitted in the block member receiving groove 32, and FIG. 3 is a plan view of an individual passage blocking member 33.

The generally semicircular blocking member 33 has a thick arcuate support portion 33a on its outer circumference, which is to be fitted into the block member receiving groove 22. The area inward of the support portion 33a provides a passage 33e leading to the treatment tool receiving socket 31 which is interrupted by a thin blocking portion 33b.

The size of the arcuate support portion 33a is just one half the circumference of the groove 32 (an angle of 180° is subtended by the arc). The blocking valve portion 33b is slightly larger than half a circle and so shaped that the side corresponding to its diameter 33c (which is hereinafter referred to simply as "diameter 33c") slightly projects beyond the straight side of the arcuate support portion 33a.

If two units of the passage blocking member 33 having the above-described structure are fitted onto the block member receiving groove 32, the blocking valve portions 33b of the two blocking members interfere with each other and their diameters 33c abut each other to become deformed as shown in FIG. 1.

Therefore, when no treatment tool is inserted, the blocking valve portions 33b which are deformed by the abutting action of the end faces of their diameters 33c ensure that the passage 33e leading to the socket 31 is tightly closed to prevent the leakage of pressure from the channel 4.

Even if the diameters 33c of the blocking valve portions 33b wear slightly due to the repeated insertion and removal of a treatment tool, the valve portions 33b maintain a sufficient closure to ensure that there will be no pressure leakage when the treatment tool is not used.

Figure 4:
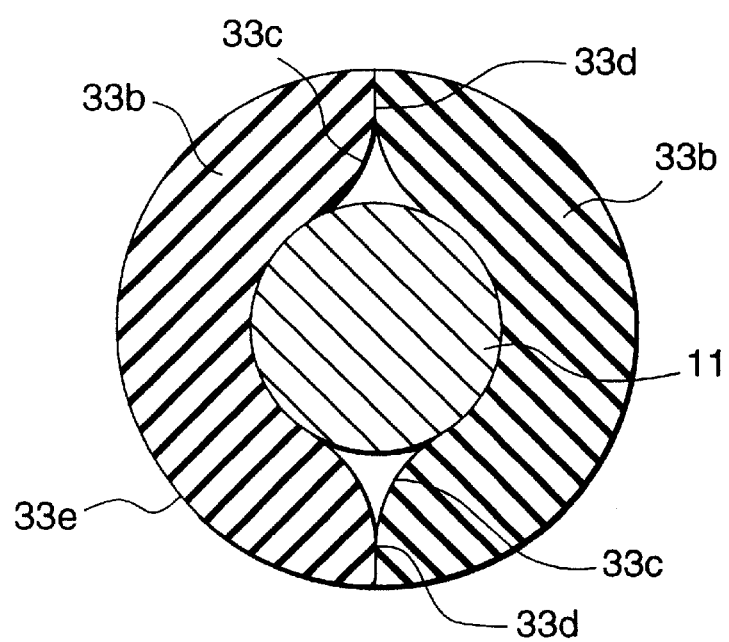
FIG. 4 is a cross-sectional sketch of the blocking valve portions with a treatment tool inserted according to the first embodiment.

If the treatment tool is inserted, the blocking valve portions 33b are elastically spread apart from each other to permit its passage. However, as shown schematically in FIG. 4, the peripheral portions 33d of the diameters 33c being spaced apart by the sheath 11 of the passing treatment tool undergo such a positive blocking action that only small gaps form and there occurs very limited pressure leakage. If the treatment tool is withdrawn, the initial closure is restored.

Figure 5:
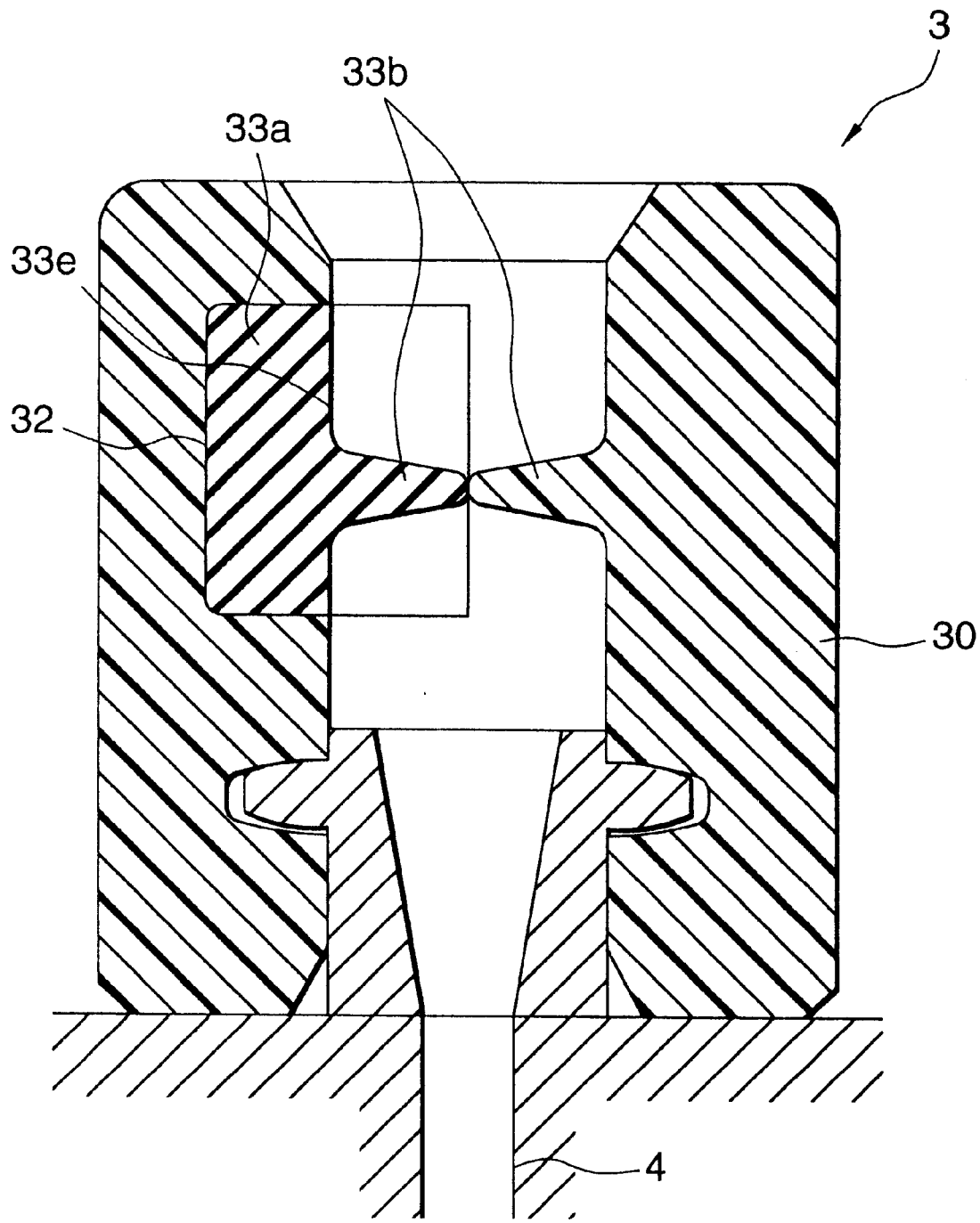
FIG. 5 shows a front section of an endoscopic forceps stopper according to a second embodiment.

FIG. 5 shows the forceps stopper 3 according to a second embodiment. One of the two blocking valve portions 33b is molded as an integral part of the stopper casing 30. Similarly to the first embodiment, the blocking member 33 having the other blocking valve portion 33b is fitted into the block member receiving groove 32 which is formed along one half the circumference of the circle. The other parts of the forceps stopper are essentially the same in the first embodiment.

Figure 6:
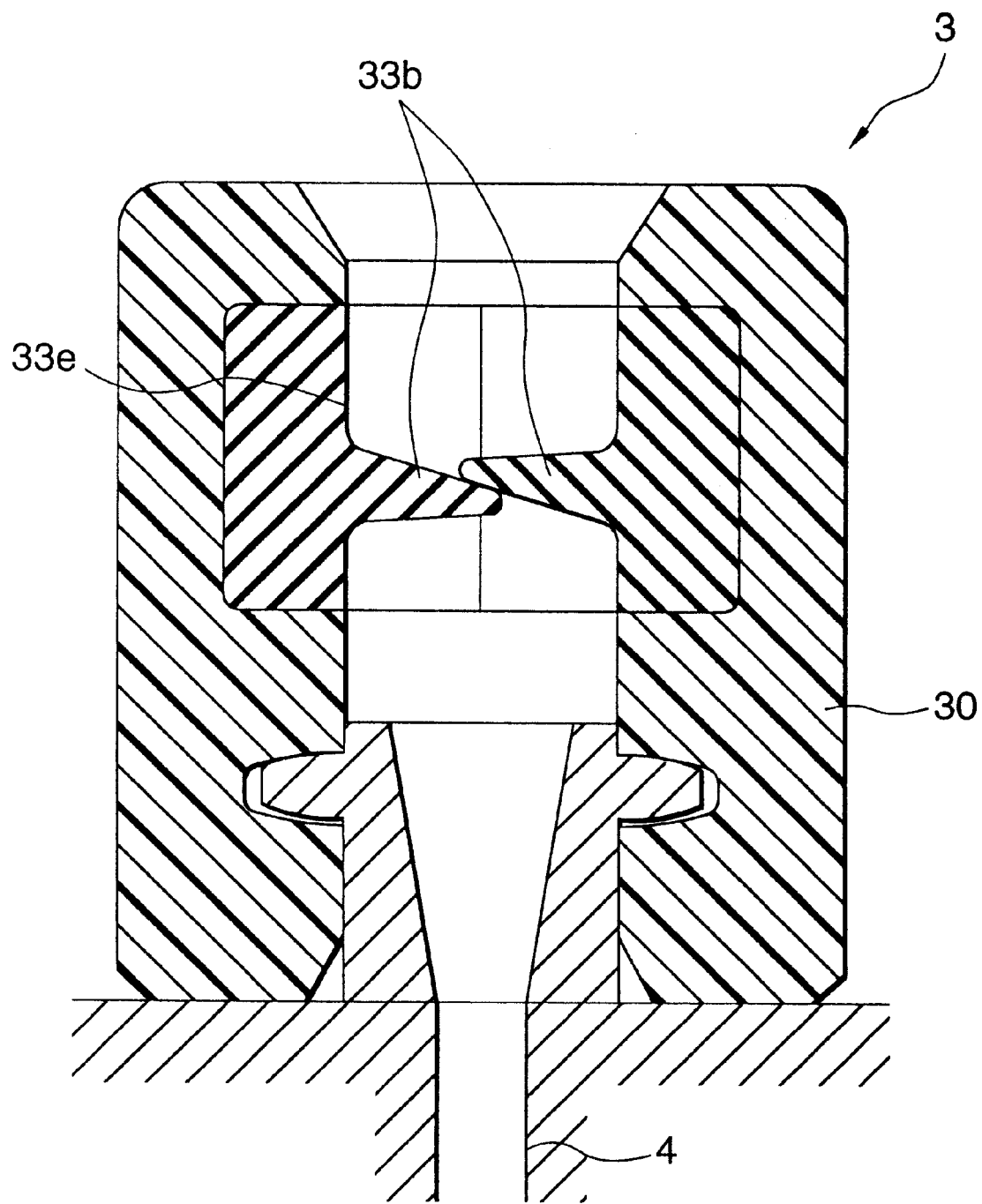
FIG. 6 shows a front section of an endoscopic forceps stopper according to a third embodiment.
Figure 7:
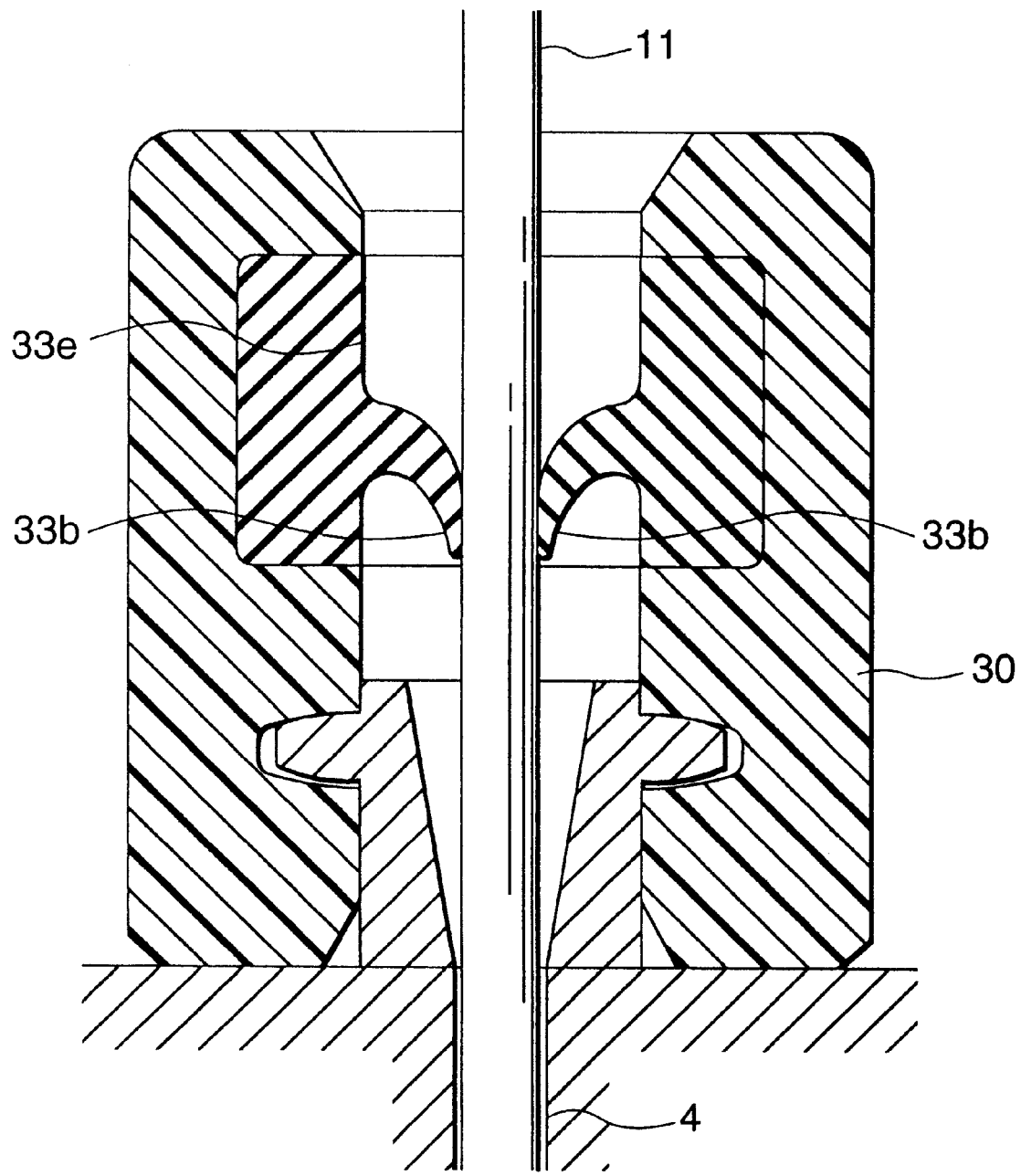
FIG. 7 shows a front section of the endoscopic forceps stopper according to the third embodiment with a treatment tool inserted.

FIG. 6 shows the forceps stopper 3 according to a third embodiment of the invention. A pair of blocking valve portions 33b are provided in such a state that their diameters abut against each other to overlap partly.

When no treatment tool is inserted, the abutting blocking valve portions 33b overlap each other and prevent the leakage of pressure from the channel 4 by ensuring tight closure of the passage 33e leading to the treatment tool receiving socket 31.

If a treatment tool is inserted, its sheath spreads apart the blocking valve portions 33b elastically. If the treatment tool is removed, the initial closure is restored.

The present invention is by no means limited to the embodiment described above and all that is needed is that a pair of generally semicircular, blocking valve portions 33b be provided in such a state that their diameters 33c abut to interfere with each other. The size, shape and other features of the two blocking valve portions 33b need not necessarily be the same.

What is claimed is:

1. An endoscopic forceps stopper comprising:

a pair of generally semicircular, passage blocking valves, each blocking valve of said pair of blocking valves being discrete from each other and made of an elastic material, said pair of blocking valves being configured to block a passage leading to an inlet of a treatment insertion channel of an endoscope;

a pair of diameter portions each affixed to a respective said blocking valve, each diameter portion of said pair of diameter portions configured to abut with each other and wherein abutting surfaces of said diameter portion engage each other when no external force is applied thereto, and are spread apart from each other elastically when a treatment tool is inserted, wherein said pair of generally semicircular, passage blocking valves are provided in such a state that the pair of diameter portions are deformed by abutting against each other.

2. The endoscopic forceps stopper according to claim 1, wherein said pair of generally semicircular, passage blocking valves are provided in such a state that the pair of said diameter portions partly overlap each other.

3. The endoscopic forceps stopper according to claim 1, wherein at least one of said pair of passage blocking valves is detachably provided.

4. The endoscopic forceps stopper according to claim 1, wherein at least one of said pair of passage blocking valves is detachably provided.

5. The endoscopic forceps stopper according to claim 2, wherein at least one of said pair of passage blocking valves is detachably provided.

6. An endoscopic forceps stopper comprising:

a pair of generally semicircular, passage blocking valves, each blocking valve of said pair of blocking valves being discrete from each other and made of an elastic material, said pair of blocking valves being configured to block a passage leading to an inlet of a treatment insertion channel of an endoscope;

a pair of diameter portions each affixed to a respective said blocking valve, each diameter portion of said pair of diameter portions configured to abut with each other and wherein abutting surfaces of said diameter portion engage each other when no external force is applied thereto, and are spread apart from each other elastically when a treatment tool is inserted, wherein each said diameter portion radially protrudes a predetermined distance beyond a respective said blocking valve, and wherein said diameter portions overlap with each other when no external force is applied thereto.

* * * * *